United States Patent [19]

Raaf et al.

[11] 4,332,791
[45] Jun. 1, 1982

[54] TOOTHPASTE ACTIVE AGAINST PLAQUE COMPRISING A COPPER COMPOUND AND A SILICA POLISHING AGENT

[75] Inventors: Helmut Raaf, Bad Schwalbach; Dieter Becker, Darmstadt-Wixhausen; Franz Frosch, Taunusstein; Helmut Harth, Mainz; Helmar R. Wagner, Darmstadt, all of Fed. Rep. of Germany

[73] Assignee: Blendax-Werke R. Schneider GmbH & Co., Fed. Rep. of Germany

[21] Appl. No.: 252,405

[22] Filed: Apr. 9, 1981

[30] Foreign Application Priority Data

Apr. 29, 1980 [EP] European Pat. Off. ........ 80102304.5

[51] Int. Cl.³ .................. A61K 7/16; A61K 7/18; A61K 7/24; A61K 33/34
[52] U.S. Cl. ............................ 424/52; 424/49; 424/54; 424/55; 424/57; 424/140; 424/143; 424/294; 424/151
[58] Field of Search .................. 424/49–58, 424/140–143, 294, 151

[56] References Cited

U.S. PATENT DOCUMENTS

| | | | |
|---|---|---|---|
| 3,044,939 | 7/1962 | Scanlan et al. | 424/55 |
| 3,070,510 | 12/1962 | Cooley et al. | 424/52 |
| 3,137,632 | 6/1964 | Schiraldi | 424/54 |
| 3,151,027 | 9/1964 | Cooley et al. | 424/52 |
| 3,175,951 | 3/1965 | Tucker et al. | 424/52 |
| 3,325,368 | 6/1967 | Wood | 424/52 |
| 3,538,230 | 11/1970 | Pader et al. | 424/52 |
| 3,662,059 | 5/1972 | Wiesner et al. | 424/52 |
| 3,689,637 | 9/1972 | Pader | 424/52 |
| 3,761,583 | 9/1973 | Gladstone | 424/54 |
| 3,804,946 | 4/1974 | Harrison et al. | 424/52 |
| 3,864,470 | 2/1975 | Watson | 424/49 |
| 3,934,000 | 1/1976 | Barth | 424/49 |
| 4,007,260 | 2/1977 | Kim | 424/52 |
| 4,048,300 | 9/1977 | Tomlinson et al. | 424/52 |
| 4,102,992 | 7/1978 | Davis | 424/49 |
| 4,108,978 | 8/1978 | Mazzanobile et al. | 424/52 |
| 4,144,321 | 3/1979 | Wason | 424/49 |
| 4,146,608 | 3/1979 | Ritchey | 424/54 |
| 4,153,680 | 5/1979 | Seybert | 424/49 |

FOREIGN PATENT DOCUMENTS 367319  5/1974  Sweden .

OTHER PUBLICATIONS

Kempf et al., Chem. Abstracts, 32, #4212(7), (1938).
Kempf et al., Chem. Abstracts, 31, #7993(8), (1937).
Schmidt, Chem. Abstracts, 55, #13654(f), (1961).
Manly, Drug & Cosmetic Industry 76(3), Mar. 1955, 326, 327, 422 to 425.
Wisotzky, J. Am. Dent. Assn. 57(6):776–800, Dec. 1958.
Opperman et al., Chem. Abstracts, 94:114641f, Apr. 13, 1981, Scand. J. Dent. Res., (1980), 88(6):476–480.
Forbes, Chem. Abstracts, 46:5662h, (1952).

*Primary Examiner*—Shep K. Rose
*Attorney, Agent, or Firm*—Linda G. Bierman; Jordan B. Bierman

[57] ABSTRACT

This invention relates to a novel toothpaste and more particularly, to a new toothpaste which includes a silica polishing agent and at least one copper compound. This toothpaste has proven effective against plaque formation on teeth but does not exhibit any of the side effects of the prior art formulations such as discoloring.

14 Claims, No Drawings

TOOTHPASTE ACTIVE AGAINST PLAQUE COMPRISING A COPPER COMPOUND AND A SILICA POLISHING AGENT

This invention generally relates to toothpaste and, more particularly, to a new toothpaste having excellent properties for the prevention of the formation of dental plaque on teeth and accordingly makes a significant contribution to the maintenance of healthy teeth and gums.

According to modern dental science, there is not doubt that dental plaque is an important factor in the development of dental caries and also parodontopathies. Therefore, a substantial part of medico-dental research is directed to discover new substances and means which will prevent plaque formation on teeth. Substantial advances have already been made in this respect. One of the most investigated compounds is 1,6-di-4'-(chlorophenyldiguanido)hexane, commonly known as "chlorhexidine". This compound not only has an outstanding effect upon bacteria which are responsible for forming dental plaque, it also adheres to the enamel and thus ensures a long-lasting action.

In spite of its undisputed success in preventing and combatting parodontopathies, chlorhexidine unfortunately has certain side-effects which although being harmless per se have hitherto apparently prevented its continuous use in tooth and mouth care preparations.

Extended use of preparations containing chlorhexidine produced discolouration of the teeth and the mucous membranes. This effect is harmless and can be eliminated mechanically, but it is cosmetically undesirable. Its use may also lead to gustatory stimulation or irritation.

More recently, various attempts have been made to discover substances which do not produce these side effects but which will still effectively prevent plaque formation on the teeth.

For example, the effectiveness of copper ions has already been discussed in this respect, as shown in AADR Abstracts 1975, No. 117 (Journal of Dental Research 1975, Special Issue A, page 74). Although compounds supplying copper ions have produced satisfactory results in the prevention of plaque formation on teeth when used in solutions according to this reference, surprisingly, it has hitherto been impossible to obtain these results with corresponding toothpastes.

Accordingly, it is an object of the present invention to overcome these disadvantages by providing a toothpaste containing copper compounds which is effective against plaque formation on teeth and which is also effective in the form of a toothpaste.

The invention relates to an improved toothpaste composition containing at least on copper compound and a polishing agent, wherein the polishing agent is composed, at least for the major part, of silica.

Further objects and advantages of the invention will appear from the following description.

Surprisingly, it has been found that by using a polishing agent which consists mainly of a silicon dioxide (silica) a toothpaste containing a copper compound is outstandingly effective against plaque formation on teeth.

Silicon dioxide polishing agents are known products and are obtained by the precipitation of silicic acids as disclosed, for example, in German Published Patent Specification Nos. 2,206,285; 2,446,038, and 2,610,207; British Patent Nos. 1,433,743 and 1,447,663, and U.S. Pat. No. 4,122,160. Examples of these compounds are commercially available under the names "Neosyl TM" or "Sident TM".

Also well suited for the purpose of this invention are the silica xerogels as described in U.S. Pat. No. 3,538,230 which have specific surfaces of between about 150 and about 800 $m^2/g$. These products are commercially available from Grace & Co. and are sold under the name "Syloid TM".

Partly dehydrated silica hydrogels, as disclosed in German Published Patent Specification Nos. 2,704,504 and 2,920,906, may also be used in toothpastes according to the present invention. Generally, average particle sizes for these polishing agents are within the usual and optimal range for this purpose, namely, between about 1 to about 20 microns and preferably, between about 3 and about 14 microns.

With the silicon dioxide polishing agents hereinbefore described, toothpastes may be obtained which are opaque, translucent or transparent. This depends upon the ratio between the water and the moisturizing agent such as glycerol, and/or sorbitol and the absence of opacifying agents, whereby the refractive index of the paste base is defined. Refractive indexes of between about 1.43 and 1.46 (20° C.) are suitable to produce transparent products.

Another group of silicon dioxide polishing agents useful within the scope of the present invention are crystalline silicas, as described in German Published Patent Specification No. 2,036,551.

A detailed study of types of silicas which are suitable for use in the toothpaste according to the present invention is provided by H. Ferch in "Chemie-Ingenieur-Technik", Vol. 48(1976), pages 922–933.

Preferably silica is the only polishing agent in a toothpaste of the present invention. However, it is possible to use other polishing agents in minor amounts, provided that these other agents represent less than 50% of the total polishing agent present in the toothpaste. These additional polishing agents must not inactivate the copper compounds present.

Examples of such additional polishing agents include powdered synthetic plastic materials such as polyvinyl chloride, polyvinyl fluoride, polymethyl methacrylate, aminoplasts such as urea- or melamine-formaldehyde-condensates (having a particle size of between about 0.5 and about 40 microns, preferably between about 2 and about 20 microns). Suitable synthetic plastic polishing agents are described in U.S. Pat. Nos. 2,130,034; 3,070,510; 3,251,800; 3,357,950 and 3,151,027, and in German Published Patent Specification No. 1,617,306.

The amount of the copper compound used in the toothpaste of this invention may be between about 0.001 and about 5% by weight, calculated on Cu, of the total toothpaste. The preferred range is from about 0.05 to about 1.5% of copper and the most preferred amount is about 0.1 to 0.5% of copper.

Suitable copper compounds which supply copper ions are, in principle, all copper compounds being toxicologically harmless, compatible with mucous membranes and, to some extent, water-soluble.

The following inorganic copper salts may be used: Copper chloride, $CuCl_2$, and the dihydrate thereof; copper fluoride, $CuF_2$, and the dihydrate thereof; copper fluorosilicate, $CuSiF_6$, and the hexahydrate thereof; copper sulphate, $CuSO_4$, and the pentahydrate thereof; copper nitrate and the tri- and hexa-hydrates thereof;

and also less popular copper salts, such as copper bromide, $CuBr_2$; copper metaborate, $Cu(BO_2)_2$; copper bromate, $Cu(BrO_3)_2$; copper chlorate; $Cu(ClO_3)_2.6H_2O$; copper iodate, $Cu(IO_3)_2$, and copper fluorophosphate, $CuPO_3F$.

Preferred copper salts of organic acids include copper acetate, copper formiate, copper benzoate, copper citrate, copper tartrate, copper lactate, copper malate, copper mandelate, copper sorbate, copper pantothenate, copper gluconate, copper phytate, copper glycerophosphate, copper cinnamate, copper butyrate, copper propionate, copper laurate, copper oxalate, copper glycinate, and copper salicylate.

As stated before, the toothpaste of the present invention contains the usual additives and compounds in addition to the silica polishing agent and one or more copper compounds.

These include moisturizers such as glycerol and other polyalcohols, for example, propylene glycol, 1,3-butanediol, and polyethylene glycols having low molecular weights. Also various sugar alcohols such as sorbitol, mannitol or xylitol may be used.

In addition to these compounds, toothpaste usually contain additional compounds such as thickeners and binding agents. Most suitable in this respect are the various cellulose derivates (for example, hydroxyalkyl celluloses, and more particularly, hydroxyethyl cellulose), vegetable gums (for example, xanthan gum, carrageen) and inorganic thickeners which are inert to copper ions. The amount of these compounds is generally between about 0.25% and 3.5% by weight of the toothpaste.

The toothpastes according to the present invention may also contain surfactants which are mainly used to produce a foaming effect which is desired by the customer. Suitable surfactants include water-soluble salts of higher alkyl sulphates or alkyl ether sulphates (e.g., sodium lauryl sulphate), aliphatic acyl amides of saturated monoaminocarboxylic acids (e.g., sodium-N-lauroyl sarcosinate), taurine fatty acid amides (e.g., sodium N-alkyl-N-myristoltauride), salts of sulphonated monoglycerides of higher fatty acids (e.g., sodium monoglyceride sulphonate), fatty acid esters of isethionic acid and salts thereof, non-ionic tensides (e.g., alkylene oxide condensates with fatty alcohols and mono or polyamines), sugar esters (e.g., sucrose monolaurate), sorbitol polyoxyethylene stearate, long-chain amine oxides (e.g., dimethyllauryl amine oxide), ampholytic tensides (e.g., betaines or long-chain alkyl amino carboxylic acids), and cationic tensides (e.g., quaternary ammonium compounds such as cetyltrimethylammonium bromide).

The amount of surfactants in the toothpaste according to the invention is between 0 and 5% by weight of the total composition.

Toothpastes usually contain aromatic and flavouring substances, preservatives, etc. These compounds are known per se and have been described in numerous publications.

In a preferred embodiment of the invention, fluorine compounds are used in amounts providing concentrations of fluorine in the paste between 0.01 and 1%, preferably between 0.1 and 0.5% by weight of the toothpaste.

Suitable compounds are particularly the various salts of monofluorophosphoric acid, especially sodium, potassium, lithium, calcium and aluminium mono- and difluorophosphates, and the various fluorides containing fluorine in ionic form, especially alkali fluorides such as sodium, lithium, potassium and ammonium fluoride, stannous fluoride, manganese fluoride, zirconium fluoride, aluminium fluoride and mixtures and addition products of these fluorides with each other or with other fluorine compounds, e.g., sodium or potassium manganese fluoride.

Other fluorides that may be used are, e.g., zinc fluoride, germanium fluoride, palladium fluoride, titanium fluoride, alkali fluorozirconates, e.g., sodium or potassium fluorozirconate, stannous fluorozirconate, fluoroborates or fluorosulphates, e.g., sodium or potassium fluorosulphate.

Fluorine and copper ions may also be released in a toothpaste according to the invention in the form of one compound, e.g. as copper fluoride, copper monofluorophosphate and copper fluorosilicate.

Organic fluorine compounds may also be used, especially known addition products from long-chain amines or amino acids and hydrogen fluoride, monoethanolamine hydrofluoride or methyltriethylammonium fluoride.

The toothpastes according to the invention may also contain further substances known per se for use in such agents, e.g. enzymes such as proteases and carbohydrases, e.g. amylase, dextranase, levanase or α-1,3-glucan-3-glucanohydrolase; tartar-preventing substances such as phosphonic acids, e.g. hydroxy-ethane-1,1-diphosphonic acid, or bisbiguanidines known for plaque-prevention and their watersoluble salts.

A detailed review of the production of dentifrice preparations and the substances used therefor is given in the monography of M. S. BALSAM and E. SAGARIN, "Cosmetics-Science and Technology", 2nd Ed., Vol. 1, pages 423 to 531 (1972).

Examples of toothpastes according to the invention are given hereinafter. Those described in Examples 1,2 and 3 are opaque, those in Examples 4,5 and 6 are transparent or translucent.

EXAMPLE 1

| | | |
|---|---|---|
| Xanthan gum | 1.00 | % by weight |
| Glycerol | 10.00 | |
| Sorbitol | 15.00 | |
| $CuSO_4 . 5 H_2O$ | 0.20 | |
| Sodium monofluorophosphate | 0.76 | |
| Sodium lauryl sulphate | 1.60 | |
| Precipitated silica (of the "Neosyl"$^R$ type) | 20.00 | |
| Titanium dioxide | 0.70 | |
| Flavour mixture | 1.00 | |
| Saccharin sodium | 0.10 | |
| Methyl p-hydroxybenzoate | 0.20 | |
| Deionized water | 49.44 | |

EXAMPLE 2

| | | |
|---|---|---|
| Carrageen | 0.50 | % by weight |
| Xanthan gum | 0.50 | |
| Glycerol | 7.50 | |
| Sorbitol | 28.00 | |
| Copper formiate . 4 $H_2O$ | 0.30 | |
| Copper fluoride ($CuF_2$) | 0.25 | |
| Sodium lauroylsarcosinate | 1.40 | |
| Precipitated silica (of the "Sident"$^R$ 3 type) | 22.50 | |
| Titanium dioxide | 0.50 | |
| Saccharin sodium | 0.10 | |
| Flavour mixture | 1.00 | |

-continued

| | |
|---|---|
| Methyl p-hydroxybenzoate | 0.10 |
| n-Propyl p-hydroxybenzoate | 0.05 |
| Deionized water | 37.30 |

EXAMPLE 3

| | | |
|---|---|---|
| Xanthan gum | 1.20 | % by weight |
| Glycerol | 15.00 | |
| Sorbitol | 12.00 | |
| Copper salicylate ($Cu(C_7H_5O_3)_2 \cdot 4 H_2O$) | 1.00 | |
| Sodium lauryl sulphate | 1.40 | |
| Silica xerogel (of the "Syloid"$^R$ AL 1 type, specific surface 800 $m^2/g$) | 16.00 | |
| Pyrogenic silica (of the "Aerosil"$^R$ type) | 3.00 | |
| Titanium dioxide | 0.50 | |
| Flavour mixture | 1.00 | |
| Saccharin sodium | 0.16 | |
| Trisodium citrate | 0.25 | |
| Ethyl p-hydroxybenzoate | 0.20 | |
| Deionized water | 48.29 | |

EXAMPLE 4

| | | |
|---|---|---|
| Hydroxyethyl cellulose | 1.10 | % by weight |
| Glycerol | 26.00 | |
| Sorbitol | 23.50 | |
| Copper fluorosilicate ($CuSiF_6 \cdot 6 H_2O$) | 0.95 | |
| Sodium lauryl sulphate | 1.40 | |
| Silica xerogel (of the "Syloid"$^R$ 74 type, surface about 290 $m^2/g$) | 20.00 | |
| Silica aerogel ("Syloid$^R$ 244", surface about 260 $m^2/g$) | 1.80 | |
| Flavour mixture | 1.10 | |
| Saccharin sodium | 0.15 | |
| Methyl p-hydroxybenzoate | 0.20 | |
| Blue dyestuff solution (C.I. No. 42051); 1% | 0.05 | |
| Alcoholic herbal extract | 0.20 | |
| Deionized water | 23.55 | |

EXAMPLE 5

| | | |
|---|---|---|
| Hydroxypropyl cellulose | 1.20 | % by weight |
| 1,3-Butanediol | 6.00 | |
| Glycerol | 23.00 | |
| Sorbitol | 20.00 | |
| Sodium lauryl sulphate (10% suspension in glycerol) | 8.50 | |
| Copper fluoride ($CuF_2 \cdot 2 H_2O$) | 0.30 | |
| Copper pantothenate | 0.80 | |
| Precipitated silica (of the "Sident$^R$3" type) | 20.00 | |
| Polyethylene glycol 600 | 2.00 | |
| Flavour mixture | 1.20 | |
| Saccharin sodium | 0.20 | |
| Red dyestuff solution (C.I. No. 16255); 1% | 0.07 | |
| Ethyl p-hydroxybenzoate | 0.13 | |
| Benzoic acid | 0.10 | |
| Tartaric acid | 0.55 | |
| Deionized water | 15.95 | |

EXAMPLE 6

| | | |
|---|---|---|
| Xanthan gum | 0.40 | % by weight |
| Glycerol | 28.00 | |
| Sorbitol (70%) | 17.00 | |
| Polyethylene glycol 300 | 3.00 | |
| Copper lactate dihydrate | 1.20 | |
| Stannous fluoride ($SnF_2$) | 0.40 | |
| Hydroxyethane-1,1-diphosphonic acid, trisodium salt | 1.25 | |

-continued

| | |
|---|---|
| Bromochlorophene | 0.05 |
| Benzoic acid | 0.15 |
| Dehydracetic acid | 0.10 |
| n-Propyl p-hydroxybenzoate | 0.05 |
| Silica xerogel (of the "Syloid$^R$ 70" type, surface about 290 $m^2/g$) | 23.50 |
| Pyrogenic silica (of the "Aerosil"$^R$ type) | 1.20 |
| Sodium lauryl ether sulphate (25% in ethanol) | 10.00 |
| Deionized water | 13.70 |

Although preferred embodiments of the invention are described and illustrated, it is to be understood that the invention is not restricted to these particular embodiments.

We claim:

1. An aqueous toothpaste composition containing at least one water-soluble copper compound and at least one polishing agent, the major part of said polishing agent being silicon dioxide.

2. A method of reducing or preventing dental plaque formation comprising applying the composition of claim 1 to a tooth surface.

3. A toothpaste composition as claimed in claim 1 wherein said polishing agent is a silicon dioxide xerogel.

4. A toothpaste composition as claimed in claim 3 wherein said silicon dioxide xerogel has a surface of between about 150 and about 800 $m^2/g$.

5. A toothpaste composition as claimed in claim 1 wherein said polishing agent is a partially dehydrated silicon dioxide hydrogel.

6. A toothpaste composition as claimed in claim 1 wherein said polishing agent is a crystalline silicon dioxide.

7. A toothpaste composition as claimed in claim 1 further including additional compatible polishing agents provided that the amount of said additional polishing agents present is less than 50% of the total amount of polishing agent present in said composition.

8. A toothpaste composition as claimed in claim 7 wherein said additional polishing agents are selected from the group consisting of powdered synthetic plastic polishing agents.

9. A toothpaste composition as claimed in claim 1 wherein the amount of copper compound present is between about 0.001% and about 5% by weight of the total composition based on the amount of copper.

10. A toothpaste composition as claimed in claim 9 wherein the amount of copper compound present is between about 0.05% and about 1.5% by weight of the total composition based on the amount of copper.

11. A toothpaste composition as claimed in claim 1 wherein said copper compound is selected from the group consisting of inorganic copper salts and copper salts of organic acids.

12. A toothpaste composition as claimed in claim 1 further including at least one compound selected from the group consisting of a moisturizer, a thickener, a binding agent, a surfactant, a flavouring agent, a preservative, and a fluorine compound.

13. A toothpaste composition as claimed in claim 11 wherein said copper compound is a water-soluble inorganic copper salt.

14. A toothpaste composition as claimed in claim 11 wherein said copper salt is at least one compound selected from the group consisting of copper citrate, copper tartrate, copper pantothenate, copper lactate, copper malate, copper mandelate, copper sorbate, copper benzoate, copper salicylate, copper gluconate, copper phytate, copper glycerophosphate, copper glycinate, and copper cinnamate.

* * * * *